United States Patent
Choi et al.

(10) Patent No.: US 9,724,361 B2
(45) Date of Patent: Aug. 8, 2017

(54) COMPOSITION FOR INHIBITING LIVER FUNCTION DETERIORATION, CONTAINING CITRUS PEEL EXTRACT OR NARIRUTIN AS ACTIVE INGREDIENT, AND METHOD FOR EXTRACTING NARIRUTIN FROM CITRUS PEEL

(71) Applicant: Korea Food Research Institute, Seongnam, Gyeonggi-Do (KR)

(72) Inventors: In Wook Choi, Seoul (KR); Yong Kon Park, Suwon (KR); Yoon Sook Kim, Seoul (KR); Hee Don Choi, Seoul (KR); Ho Young Park, Seoul (KR)

(73) Assignee: Korea Food Research Institute, Seongnam, Gyeonggi-do (KR)

( * ) Notice: Subject to any disclaimer, the term of this patent is extended or adjusted under 35 U.S.C. 154(b) by 0 days.

(21) Appl. No.: 14/229,352

(22) Filed: Mar. 28, 2014

(65) Prior Publication Data

US 2014/0364382 A1  Dec. 11, 2014

Related U.S. Application Data

(63) Continuation of application No. PCT/KR2011/010362, filed on Dec. 30, 2011.

(30) Foreign Application Priority Data

Sep. 30, 2011 (KR) .................... 10-2011-0099877

(51) Int. Cl.
| | |
|---|---|
| A23C 9/133 | (2006.01) |
| A23L 1/30 | (2006.01) |
| A61K 31/7048 | (2006.01) |
| A61K 36/752 | (2006.01) |
| C07H 1/08 | (2006.01) |
| C07H 17/07 | (2006.01) |
| A23L 33/105 | (2016.01) |

(52) U.S. Cl.
CPC .......... *A61K 31/7048* (2013.01); *A23C 9/133* (2013.01); *A23L 33/105* (2016.08); *A61K 36/752* (2013.01); *C07H 1/08* (2013.01); *C07H 17/07* (2013.01); *A61K 2236/30* (2013.01)

(58) Field of Classification Search
None
See application file for complete search history.

(56) References Cited

U.S. PATENT DOCUMENTS

2010/0016246 A1* 1/2010 Benavente-Garcia Garcia ......... A21D 2/36 514/27

FOREIGN PATENT DOCUMENTS

| KR | 10-2007-0078167 A | 7/2007 |
|---|---|---|
| KR | 10-2011-0061795 A | 6/2011 |
| WO | WO 2010080245 A1 * | 7/2010 |

OTHER PUBLICATIONS

Mata-Bilbao, British Journal of Nutrition (2007), 98, 86-92.*
Cha, Jae-Young et al., "Biofunctional Activities of Citrus Flavonoids", Jrl. of the Korean Society for Applied Biological Chemistry, 2001, vol. 44, No. 2, pp. 122-128.
Son, Heung-Soo et al., "Isolation, Purification and Hypotensive Effect of Bioflavonoids in Citrus sinensis", Jrl. of the Korean Society of Food Science and Nutrition, 1992, vol. 21, No. 2, pp. 136-142.
Korean Office Action dated Apr. 12, 2013 in corresponding Korean Application No. 10-2011-0099877 (with English translation).
International Search Report mailed Sep. 26, 2012 for corresponding PCT International Application No. PCT/KR2011/010362.
Author Mohammad Azam Khan Title of publication—Muheet-e-Azam vol. II ( Part I) (19th century AD) Page(s) being submitted—04(p. 04-07) ( Ref.p. of publication:22 ) Publication Date—1895 AD Publisher—Matba Nizami Place of Publication—Kanpur, India.†
Author Ziya Al-Din Abdullah Ibn Al-Baitar Title of publication—Al-Jaam'e-li-Mufradaat-al-Advia-wal-Aghzia vol. IV (13th century AD) Page(s) being submitted—05 (p. 08-12) ( Ref.p. of publication:120 ) Publication Date—1874 AD Publisher—Matba Amra Cairo Place of Publication—Egypt.†
Author—Title of publication—Ayurveda Sarasamgrahah—Page(s) being submitted—06 (p. 13-18) ( Ref.p. of publication:167 ) Publication Date—Edn. 2003 Publisher—Shri Baidyanath Ayurveda Bhavan Place of Publication—Calcutta, India.†

\* cited by examiner
† cited by third party

*Primary Examiner* — Layla Berry
(74) *Attorney, Agent, or Firm* — Mintz Levin Cohn Ferris Glovsky and Popeo, P.C.; Kongsik Kim

(57) ABSTRACT

The present invention relates to a pharmaceutical composition for treating liver diseases, containing a narirutin extract of citrus peel extract or narirutin as an active ingredient. The extract or narirutin decreases cholesterol levels and fat levels in liver tissue, and thus can be utilized as a composition or food for preventing and treating liver diseases. In addition, the present invention relates to a method for extracting narirutin from citrus peel, and a method for preparing citrus fermented milk using the same.

5 Claims, 7 Drawing Sheets

COMPOSITION FOR INHIBITING LIVER FUNCTION DETERIORATION, CONTAINING CITRUS PEEL EXTRACT OR NARIRUTIN AS ACTIVE INGREDIENT, AND METHOD FOR EXTRACTING NARIRUTIN FROM CITRUS PEEL

CROSS-REFERENCE TO RELATED APPLICATIONS

This application is a continuation of International Application No. PCT/KR2011/010362 filed on Dec. 30, 2011, which claims priority to Korean Application No. 10-2011-0099877 filed on Sep. 30, 2011. The disclosures of the above patent applications are incorporated herein by reference in their entirety.

TECHNICAL FIELD

The present invention relates to a composition for preventing and treating liver diseases, the composition containing a narirutin extract, which is one of citrus-derived flavonoids, as an active ingredient and a method for extracting narirutin from citrus peel.

BACKGROUND ART

Modern people have a strong tendency to relieve stress from work and life by habitual drinking and smoking. Particularly, constant overeating and binge eating and the accompanying excessive drinking gradually increase the incidence of liver-related diseases such as fatty liver and the like. The liver is the heart of all nutritional metabolism, and a vital organ which is responsible for maintaining homeostasis in the body and performing a buffer function. The fat accumulated in the liver is due to food intake, the inflow from adipose tissues, or fat synthesis in the liver itself. The fatty liver is caused by the inflow of fat from the adipose tissues to the liver in the case of drinking a large quantity of alcohol in a short period of time, and by fat synthesis in the liver itself in the case of chronic drinking. Fatty liver produces symptoms such as chronic fatigue, malaise, loss of appetite, indigestion, and bad hangovers. Severe alcoholic fatty liver may produce bad hangovers, extreme fatigue after drinking, and the like.

Alcoholic liver disease is different from toxipathic hepatitis, and thus is generally referred to differently from toxipathic hepatitis. Alcohol that is ingested is not stored in the body, but about 90-98% of alcohol is oxidized into acetaldehyde by alcohol dehydrogenase, again oxidized into acetic acid by aldehyde dehydrogenase, and finally oxidized into carbon dioxide and water. In this procedure, fatty acids as concomitant products are accumulated in the liver, but acetaldehyde as an intermediate product directly damages liver cells due to its hepatotoxicity.

Mallory's bodies and expandable degeneration may be confirmed as characteristic findings of alcoholic liver diseases, and the liver state in this case is called fatty liver.

After that, leukocytes gather into hepatic lobules to remove debris of nectrotized liver cells, causing inflammation, resulting in alcoholic hepatitis. This stage may be returned to normal conditions by simply just stopping alcohol consumption. However, when this hepatitis lasts for a long time, fibrosis occurs within the liver tissue. If the fibrosis progression is widespread, the liver tissue is replaced by connective tissue instead of normal hepatocytes, finally leading to liver cirrhosis. Once the fibrosis progression occurs in the liver tissue, the tissue cannot be returned to completely normal conditions despite being recovered, resulting in irreversible liver damage in which the already formed scar tissue remains permanently.

Meanwhile, many flavonoid compounds have been known to be useful in the improvement of physical function through various actions, and many endeavors to develop action mechanisms and uses of useful flavonoid compounds have been made. Narirutin, which is one of flavonoid compounds, is a flavonoid material present in citrus, and has been known to have a blood pressure lowering effect (Son et al., J. Korean Soc. Food Nurt., 1992, 21(2) pp. 136-142). However, the liver dysfunction inhibitory effect of narirutin has not been known.

SUMMARY OF THE INVENTION

Therefore, the present invention has been made in view of the above-mentioned problems, and an aspect of the present invention is to provide a pharmaceutical composition for treating liver diseases, containing a citrus peel extract or narirutin, as an active ingredient.

Another aspect of the present invention is to provide a food composition for improving liver diseases, containing a citrus peel extract or narirutin, as an active ingredient.

Still another aspect of the present invention is to provide a method for extracting narirutin from citrus peel.

In accordance with an aspect of the present invention, there is provided a pharmaceutical composition for treating liver diseases, the composition including a citrus peel extract as an active ingredient. The liver disease may be induced by liver damage. The liver disease may be an alcoholic liver disease. The citrus peel extract may be orally administered. The citrus peel extract may be a tablet, a hard capsule, or a soft capsule.

In accordance with another aspect of the present invention, there is provided a pharmaceutical composition for treating liver diseases, the composition including narirutin as an active ingredient. The liver disease may be an alcoholic liver disease.

In accordance with another aspect of the present invention, there is provided a food composition for improving liver diseases, the composition including a citrus peel extract or narirutin as an active ingredient. The composition may be fermented milk.

In accordance with another aspect of the present invention, there is provided a method for extracting narirutin from citrus peel, the method including sonicating citrus peel in 60% to 80% alcohol solvent having 20 to 40 volumes of the citrus peel for 15 to 40 minutes. Here, in the sonicating of the citrus peel, the citrus peel may be a lyophilized powder. Here, in the sonicating of the citrus peel, the alcohol solvent may have 30 volumes of the citrus peel or citrus flesh. The alcohol solvent may be 70% ethanol. The sonicating may be performed for 30 minutes. The narirutin may be further extracted by using ethyl acetate.

The citrus peel narirutin extract or narirutin of the present invention functions to lower cholesterol and fat level in liver tissue, and thus can be utilized as a composition or food for preventing and treating liver diseases.

DETAILED DESCRIPTION OF THE INVENTION

Hereinafter, components and technical features of the present invention will be described in more detail with reference to the following examples. However, the following examples are provided merely to illustrate the present invention and not to restrict the scope of the present invention. All documents cited herein are incorporated herein by reference in their entirety.

EXAMPLES

Example 1

Preparation of Narirutin-Containing Extract from Citrus Peel

A primary extract (A) containing narirutin was obtained from citrus peel using sonication, and a tertiary extract (C) having a high narirutin content was obtained using ethyl acetate.

1.1 Preparation of Primary Citrus Peel Extract Using Sonication (Sonication Step)

Extraction conditions and results were shown in Table 1 below. Herein, the conventional reflux extraction process for a comparative example was conducted by preparing a citrus peel powder through separation, drying at 50° C., and pulverization of citrus peel, and then adding 70% ethanol in an amount (mass/volume) of 20 volumes of the citrus peel powder, followed by extraction at 80° C. for 3 hours.

TABLE 1

|  |  | Sovent | | | | | Narirutin |
|---|---|---|---|---|---|---|---|
|  |  | % ethanol | Volume | Time (min) | Temperature (° C.) | Yield (%) | content (%) |
| Sonication extraction | U-EtOH-A | 0% | 20x | 10 | 30 | 39.80 | 4.0 |
|  | U-EtOH-B | 35% | 20x | 10 | 30 | 35.71 | 4.6 |
|  | U-EtOH-C | 70% | 20x | 10 | 30 | 37.02 | 5.3 |
|  | U-EtOH-D | 95% | 20x | 10 | 30 | 20.59 | 5.1 |
|  | U-time-A | 70% | 20x | 10 | 30 | 37.02 | 5.3 |
|  | U-time-B | 70% | 20x | 20 | 30 | 38.45 | 5.3 |
|  | U-time-C | 70% | 20x | 30 | 30 | 38.91 | 6.4 |
|  | U-time-D | 70% | 20x | 60 | 30 | 40.21 | 6.4 |
|  | U-Sol-A | 70% | 10x | 10 | 30 | 27.24 | 5.5 |
|  | U-Sol-B | 70% | 20x | 10 | 30 | 37.02 | 5.3 |
|  | U-Sol-C | 70% | 30x | 10 | 30 | 44.32 | 5.4 |
|  | U-Sol-D | 70% | 40x | 10 | 30 | 45.12 | 5.2 |
| Conventional reflux extraction | Conventional reflux extraction | 70% | 30x | 180 | 80 | 43.96 | 5.1 |

As shown in Table 1 above, the extraction yield and purity of narirutin in the extract were almost the same as those from the general reflux extraction process, but the energy consumption was about 40% that of the general reflux extraction process. Table 1 above indicated that the treatment with 70% ethanol in an amount of about 30 volumes for 30 minutes was the most effective. Therefore, a primary citrus peel extract was obtained by adding, as a solvent, 70% alcohol in an amount of 30 volumes of the citrus peel powder and performing sonication under conditions of an intensity of 20 kHz, a temperature of 30° C. and an amplitude of 80%. Then, the narirutin content in the primary citrus peel extract was measured.

1.2 Preparation of Secondary and Tertiary Extracts Having Increased Narirutin Content (Extraction Step with Water and Extraction Step with Ethyl Acetate)

Figure 1:
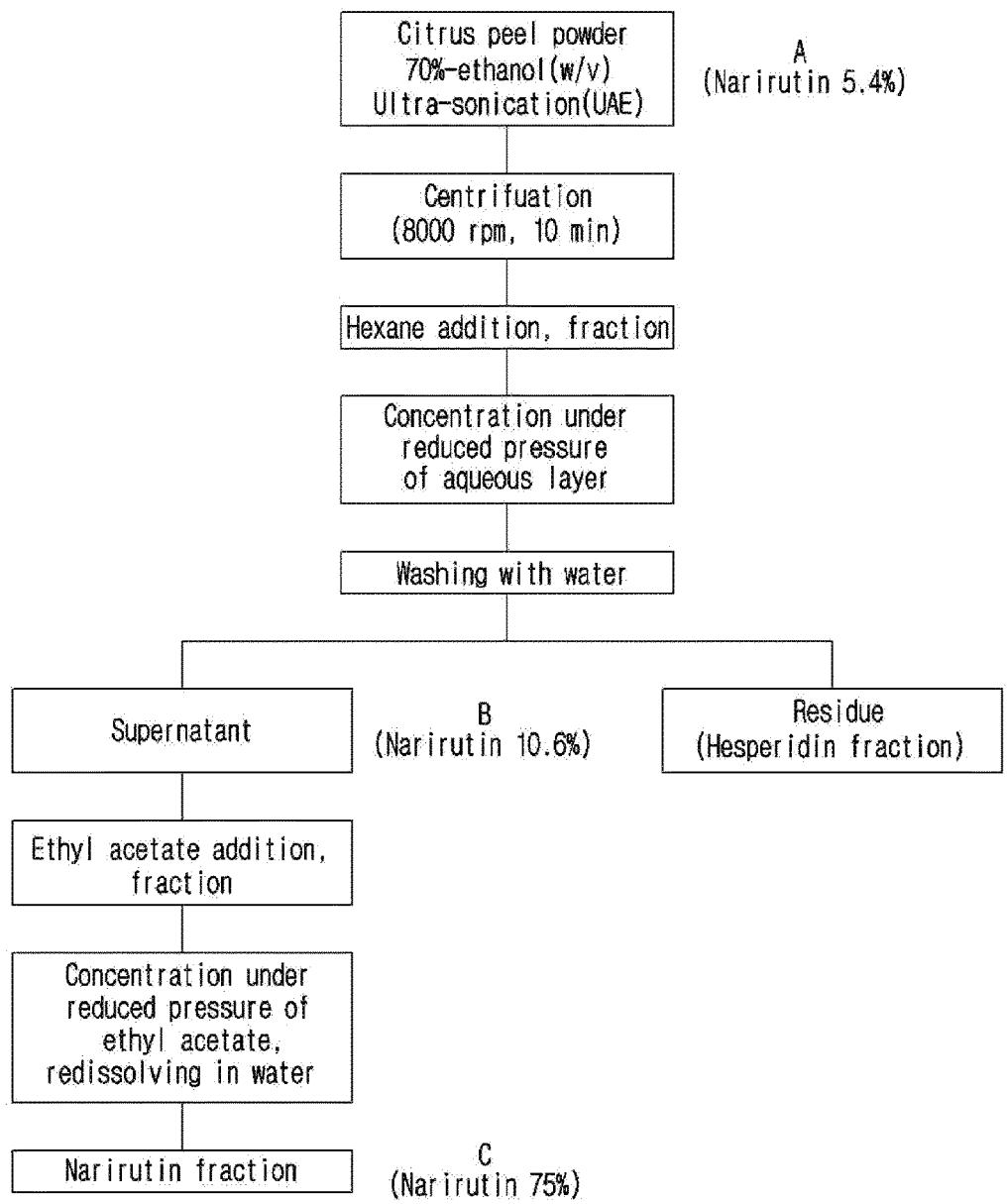
FIG. 1 is a flowchart showing the extraction of narirutin from citrus peel according to an embodiment of the present invention. Here, A represents a primary citrus peel extract; B a secondary citrus peel extract; and C a tertiary citrus peel extract.

The primary citrus peel extract obtained using sonication as in Section 1.1 was subjected to processes as shown in FIG. 1, thereby obtaining a secondary citrus peel extract and a tertiary citrus peel extract. Specifically, the primary citrus peel extract obtained using sonication was centrifuged at 8000 rpm for 10 minutes. The supernatant was fractioned by addition of hexane. The aqueous layer was concentrated under reduced pressure, and then again dissolved in water, thereby obtaining a secondary citrus peel extract (B) having a purity of 10% or higher. The secondary citrus peel extract was fractioned by addition of ethyl acetate. The ethyl acetate layer was concentrated under reduced pressure, and then again dissolved in water, thereby obtaining a tertiary citrus peel extract (C) having a narirutin purity of 75%.

Example 2

Alcoholic fatty liver inhibitory effect of Citrus Peel Extract

In the present example, rats were orally administered with the secondary citrus peel extract (B) obtained from citrus peel together with 36% alcohol, to investigate the effect of the citrus peel extract on the liver disease caused by alcohol ingestion.

To investigate the alcoholic fatty liver inhibitory effect of the citrus peel extract, 8-week old male SD rats were fed a secondary citrus peel extract diet for 6 weeks together with 70 μl of 36% ethanol every day or narirutin corresponding to 20 mg (low narirutin) or 40 mg (high narirutin) together with the same ethanol every day. The secondary citrus peel extract was diluted with an appropriate amount of DW such that the narirutin concentration was 2%. The diluted solution was added to the Lieber-DeCarli diet to have 1.4% (low narirutin) or 2.8% (high narirutin). The diet period was 6 weeks.

2.1. Effects of Narirutin Supply on Blood Fat Levels

Effects of 6-week narirutin supply on triglyceride, cholesterol, GOT, and GPT levels were shown in Table 2 below.

TABLE 2

| Lipids | Control | Ethanol | Low Narirutin | High Narirutin |
| --- | --- | --- | --- | --- |
| Triglycerides, mg/dL | 61.85 ± 14.56$^b$ | 85.52 ± 22.80$^a$ | 41.30 ± 14.72$^c$ | 20.97 ± 6.73$^d$ |
| Total cholesterol(C), mg/dL | 63.71 ± 5.54$^c$ | 94.14 ± 13.46$^a$ | 90.05 ± 10.59$^a$ | 77.63 ± 9.56$^b$ |
| HDL-C, mg/dL | 36.49 ± 2.42$^b$ | 51.76 ± 9.70$^a$ | 51.28 ± 6.92$^a$ | 42.05 ± 7.96$^b$ |
| non HDL-C, mg/dL | 27.22 ± 5.35$^b$ | 42.37 ± 7.97$^a$ | 38.78 ± 7.85$^a$ | 35.58 ± 6.15$^a$ |

[1] Values are presented as the mean ± SD (n = 8).
[2] Means in same rows with different superscript were significantly different ($p < 0.05$).
[3] Abbreviation: GOT, glutamate-oxaloacetate transaminase; GPT, glutamate-pyruvate transaminase.

As shown in Table 2 above, the ingestion of the narirutin extract lowered the blood fat levels in rats. The cholesterol level was also reduced in the high-narirutin-fed group. Specifically, the triglyceride level was further lowered in the high-narirutin-fed group and the low-narirutin-fed group than in the ethanol-fed group and the control group. The cholesterol level was higher in the high-narirutin-fed group than in the control group, but significantly lower in the high-narirutin-fed group than in the ethanol group.

2.2 Effect of Narirutin Supply on Fat Content Change in Liver Tissue

To investigate the effect of narirutin supply on the liver tissue, tocopherol level, cholesterol level, liver weight, and total lipid level in the liver were measured, and the results were shown in Table 3 below.

TABLE 3

| | Control | Ethanol | Low Narirutin | High Narirutin |
| --- | --- | --- | --- | --- |
| Tocopherol (nmol/g liver) | 127.8 ± 28.9 | 167.6 ± 33.9 | 143.8 ± 221.8 | 131.7 ± 39.7 |
| Total Cholesterol (umol/g liver) | 13.3 ± 2.1$^b$ | 19.6 ± 2.3$^a$ | 19.3 ± 2.4$^a$ | 16.0 ± 4.2$^{ab}$ |

TABLE 3-continued

|  | Control | Ethanol | Low Narirutin | High Narirutin |
|---|---|---|---|---|
| Liver weight (g) | 10.8 ± 0.9$^a$ | 10.0 ± 0.7$^{ab}$ | 10.7 ± 0.4$^a$ | 9.5 ± 0.7$^b$ |
| total lipid (mg/g) | 165.8 ± 15.2$^b$ | 227.0 ± 21.5$^a$ | 220.2 ± 27.6$^a$ | 186.9 ± 26.6$^b$ |

*Values are presented as the mean ± SD (n = 8).
$^a$Means in same rows with different superscript were significantly different (p < 0.05).

As shown in Table 3 above, α-tocopherol, total cholesterol, and total lipid levels were observed to be significantly increased in the liver tissue of the ethanol-fed group as compared with the control group (P<0.05). In addition, the groups fed ethanol and narirutin extract at the same time were observed to have low levels of α-tocopherol, total cholesterol, and total lipid as compared with the ethanol-fed group, and especially, the levels were significantly low in the high-narirutin-fed group (P<0.05). Therefore, the supply of narirutin to the diet for rats with alcoholic fatty liver can reduce the occurrence of alcohol-induced diseases associated with total lipid and total cholesterol of the liver tissue.

Table 4 below shows observation results of the fatty acid composition change.

triglyceride and this action can prevent the formation of alcoholic fatty liver by the ingestion of narirutin.

2.3 Hepatic Histology Through Liver Tissue Photographing

Figure 2:
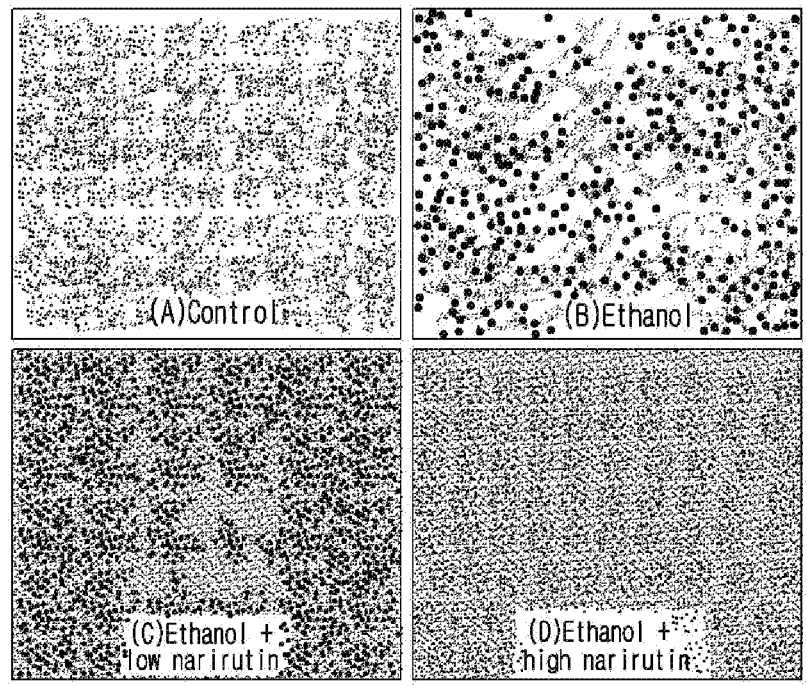
FIG. 2 shows histological evaluation results of lipid droplets in rat liver tissue due to the narirutin extract administration according to an embodiment of the present invention.
Figure 2:
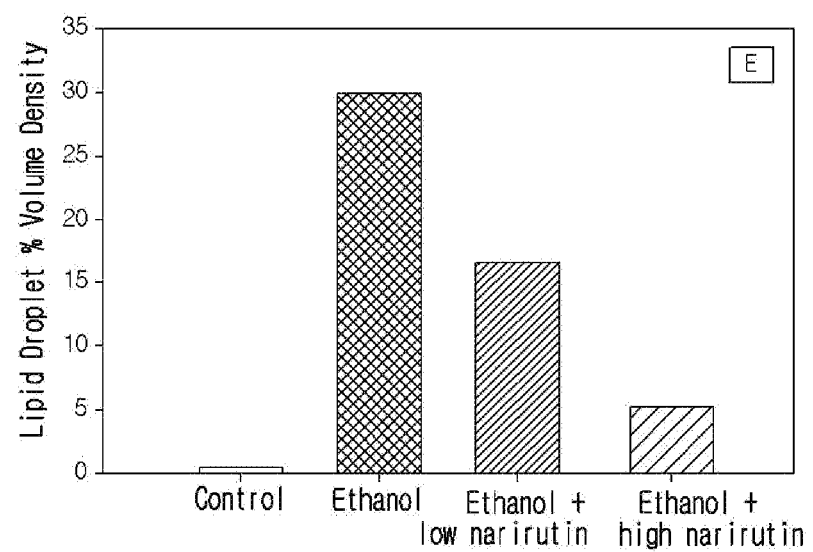

Histological evaluation for determining fatty liver symptoms has been known to be a direct and accurate method, and the results were shown in FIG. 2 (200-fold magnification; red spots indicating lipid droplets accumulated in the liver tissue cells stained with oil red).

The amount of lipid droplets that appear red was small as show in FIG. 2(A), but an increase in lipid droplets (lipid staying in the liver) as shown in FIG. 2(B) due to the supply

TABLE 4

| | (umol/g liver) | | | |
|---|---|---|---|---|
| Lipid | Control | EtOH | EtOH + Low Narirutin | EtOH + High Narirutin |
| Cholesterol ester | | | | |
| 16:0 | 2.73 ± 0.42$^a$ | 2.45 ± 0.82$^{ab}$ | 1.96 ± 0.24$^{bc}$ | 1.78 ± 0.63$^c$ |
| 18:0 | 0.45 ± 0.08$^b$ | 0.53 ± 0.11$^a$ | 0.49 ± 0.03$^{ab}$ | 0.41 ± 0.06$^b$ |
| 18:1 | 5.06 ± 1.48$^b$ | 10.41 ± 3.22$^a$ | 10.53 ± 2.52$^a$ | 7.83 ± 2.95$^a$ |
| 18:2 | 1.93 ± 0.61$^b$ | 3.46 ± 0.86$^a$ | 3.50 ± 0.77$^a$ | 2.74 ± 1.00$^{ab}$ |
| 20:4 | 0.93 ± 0.34$^b$ | 1.55 ± 0.39$^a$ | 1.70 ± 0.33$^a$ | 1.38 ± 0.49$^a$ |
| Triglyceride | | | | |
| 16:0 | 13.77 ± 3.83$^b$ | 24.68 ± 10.69$^a$ | 20.65 ± 5.93$^{ab}$ | 17.83 ± 3.85$^{ab}$ |
| 18:0 | 0.95 ± 0.26$^c$ | 1.89 ± 0.62$^a$ | 1.73 ± 0.41$^{ab}$ | 1.40 ± 0.13$^b$ |
| 18:1 | 28.02 ± 8.38$^c$ | 58.00 ± 22.60$^a$ | 50.47 ± 14.43$^{ab}$ | 39.11 ± 6.03$^{bc}$ |
| 18:2 | 17.36 ± 5.55$^b$ | 36.50 ± 14.02$^a$ | 33.23 ± 9.40$^a$ | 27.48 ± 4.01$^a$ |
| 20:4 | 1.71 ± 0.57$^b$ | 4.61 ± 1.55$^a$ | 5.42 ± 1.57$^a$ | 4.56 ± 0.60$^a$ |
| 22:6 | 0.15 ± 0.05$^b$ | 1.09 ± 0.40$^a$ | 1.29 ± 0.44$^a$ | 1.19 ± 0.19$^a$ |
| Phospholipid | | | | |
| 16:0 | 14.57 ± 4.53 | 13.85 ± 1.08 | 13.68 ± 0.71 | 14.69 ± 0.61 |
| 18:0 | 20.08 ± 6.18$^b$ | 23.58 ± 1.24$^{ab}$ | 22.66 ± 1.53$^{ab}$ | 24.42 ± 1.07$^a$ |
| 18:1 | 1.42 ± 0.49 | 1.52 ± 0.21 | 1.51 ± 0.15 | 1.49 ± 0.10 |
| 18:2 | 7.76 ± 5.63 | 7.85 ± 0.56 | 6.88 ± 0.63 | 6.74 ± 0.48 |
| 20:4 | 24.38 ± 7.51 | 25.39 ± 1.48 | 25.70 ± 2.07 | 26.16 ± 2.25 |
| 22:6 | 3.58 ± 1.13 | 4.01 ± 0.36 | 3.92 ± 0.42 | 4.40 ± 0.92 |
| Free fatty acid | | | | |
| 16:0 | 2.53 ± 0.29$^a$ | 2.42 ± 0.34$^{ab}$ | 2.17 ± 0.21$^b$ | 2.29 ± 0.13$^{ab}$ |
| 18:0 | 1.57 ± 0.09$^b$ | 1.76 ± 0.21$^a$ | 1.65 ± 0.10$^{ab}$ | 1.73 ± 0.09$^a$ |
| 18:1 | 1.21 ± 0.28$^{ab}$ | 1.28 ± 0.19$^a$ | 1.02 ± 0.14$^b$ | 1.02 ± 0.19$^b$ |
| 18:2 | 0.77 ± 0.16$^{ab}$ | 0.91 ± 0.17$^a$ | 0.67 ± 0.10$^b$ | 0.78 ± 0.13$^{ab}$ |
| 18:3 | 0.02 ± 0.01$^a$ | 0.02 ± 0.01$^a$ | 0.01 ± 0.00$^b$ | 0.01 ± 0.00$^{ab}$ |
| 20:4 | 0.27 ± 0.07$^c$ | 0.52 ± 0.07$^b$ | 0.48 ± 0.09$^b$ | 0.68 ± 0.08$^a$ |
| 22:6 | 0.03 ± 0.01$^c$ | 0.08 ± 0.01$^b$ | 0.08 ± 0.02$^b$ | 0.11 ± 0.02$^a$ |

The contents of respective fatty acids were higher in the alcohol-fed group than in the other groups, which were the same with the results obtained by measuring the liver fat content. Especially, it can be seen that the ingestion of the narirutin extract inhibits the conjugation of oleic acid into of alcohol for 6 weeks was observed under a microscope. However, when narirutin was supplied at low and high concentrations together with the same amount of alcohol for 6 weeks, the amount of lipid accumulated in the liver tissue was visually found to be sharply decreased. As a result of measuring the percent of lipid droplets in the liver tissue by using the ImageJ software program (nih, http://rsb.info.nih.gov/ij/), groups fed narirutin together with alcohol were found to efficiently inhibit the formation of fatty liver due to alcohol ingestion in a dose-dependent manner.

The above results suggested that the ingestion of the secondary citrus peel extract inhibits the conjugation of fatty acid into triglyceride in the liver, resulting in inhibiting the formation of fatty liver.

Example 3

Alcoholic Liver Disease Inhibitory Effect of Citrus Peel Extract

In the present example, ICR mice (Central Experimental Animal Center) were orally administered with the tertiary citrus peel extract (C, purity: 75%) together with 40% alcohol, to investigate the effect of the citrus peel extract on the liver disease caused by alcohol ingestion. The dose and dosing period of alcohol were increased as compared with Example 2 to induce the alcoholic liver disease.

3.1 Effect of Narirutin Administration on Increases in Body Weight and Liver Weight Respective mouse groups were orally administered with alcohol and the tertiary citrus peel narirutin for weeks, and then weekly measurement results of body weight and liver weight were shown in Table 5 below.

TABLE 5

(Unit: g)

| Week (wk) | Control | Ethanol | Narirutin (150 mg/kg) | Narirutin (300 mg/kg) |
|---|---|---|---|---|
| 0 wk | 27.26 ± 0.11 | 28.23 ± 0.43 | 28.65 ± 0.22 | 27.72 ± 0.31 |
| 1 wk | 36.97 ± 0.50 | 37.87 ± 0.35 | 36.90 ± 0.39 | 36.95 ± 0.64 |
| 2 wk | 38.64 ± 0.37 | 37.19 ± 0.72 | 38.02 ± 1.04 | 37.09 ± 0.93 |
| 3 wk | 39.72 ± 0.54 | 39.54 ± 0.78 | 39.45 ± 0.57 | 38.54 ± 0.65 |
| 4 wk | 40.78 ± 0.52 | 40.22 ± 0.39 | 39.84 ± 0.57 | 40.03 ± 0.69 |
| 5 wk | 41.83 ± 0.68 | 41.95 ± 1.07 | 40.82 ± 0.60 | 40.92 ± 0.95 |
| 6 wk | 42.70 ± 0.49 | 42.55 ± 0.60 | 42.02 ± 0.60 | 42.35 ± 1.11 |
| 7 wk | 43.97 ± 0.92 | 43.19 ± 0.41 | 42.91 ± 0.72 | 43.27 ± 0.13 |
| 8 wk | 44.18 ± 0.95 | 44.50 ± 0.75 | 42.90 ± 0.75 | 42.74 ± 0.78 |

As shown in Table 5 above, the liver weights of the experimental animals after the completion of the experiment were found to show a tendency to increase more in the ethanol-administered group than in a normal diet-fed group.

Meanwhile, the liver weights of the mice fed ethanol and narirutin extract were showed to have a similar level to those of the normal diet-fed group (Table 6).

TABLE 6

| Treatment group | Liver weight (g) |
|---|---|
| Control | 1.54 ± 0.02$^a$ |
| Ethanol | 1.59 ± 0.02$^b$ |
| Low-narirutin | 1.57 ± 0.02$^a$ |
| High-narirutin | 1.54 ± 0.03$^a$ |

3.2 Effect of Narirutin Supply on Blood Fat Levels

To evaluate the liver protection effect of narirutin, GOT and GPT activities were measured in a long-term ethanol-induced alcoholic hepatotoxicity animal model, and the results were shown in Table 7 below. GOT and GPT levels are indicators of liver damage. When hepatocellular dysfunction occurs due to alcohol, GOT and GPT are released into the blood, causing levels of these enzymes to rise, which indicates that severe hepatocellular damage is being developed.

TABLE 7

|  | Control | Ethanol | Narirutin (150 mg/kg) | Narirutin (300 mg/kg) |
|---|---|---|---|---|
| GOT$^b$(U/L) | 26.2 ± 1.3$^a$ | 35.3 ± 1.9$^b$ | 29.2 ± 1.9$^b$ | 28.9 ± 1.1$^a$ |
| GPT$^c$(U/L) | 13.8 ± 0.7$^a$ | 29.2 ± 1.3$^b$ | 13.5 ± 0.8$^a$ | 13.8 ± 1.0$^a$ |

As shown in Table 7 above, GOT activities were 26.2 ±1.3 U/L, 35.3±1.9 U/L, 29.2±1.9 U/L, and 28.9±1.1 U/L in a normal group, an ethanol group, an ethanol+narirutin (150 mg/kg)-administered group, and an ethanol+narirutin (300 mg/kg)-administered group, respectively. GOT activity was significantly higher in the ethanol group than in the control group, and was lower in the ethanol+narirutin (150 mg/kg)-administered group and the ethanol+narirutin (300 mg/kg)-administered group than in the ethanol group. In addition, GPT activities were 13.8±0.7 U/L, 29.2±1.3 U/L, 13.5±0.8 U/L, 13.8±1.0 U/L in the normal group, the ethanol group, the ethanol+narirutin (150 mg/kg)-administered group, and the ethanol+narirutin (300 mg/kg)-administered group, respectively. The GPT activity was significantly higher in the ethanol group than in the normal group, and was lower in the ethanol+narirutin (150 mg/kg)-administered group and the ethanol +narirutin (300 mg/kg)-administered group than in the ethanol group.

According to the present experiment results, both GOT and GPT activities were significantly higher in the ethanol group than in the normal group, indicating that chronic alcohol administration induced the liver damage, and GOT and GPT activities were lower in the ethanol+narirutin (150 mg/kg)-administered group and the ethanol +narirutin (300 mg/kg)-administered group than in the ethanol group, indicating that the liver damage was inhibited.

3.3 Effect of Narirutin Supply on Fat Content Change in Liver Tissue

From the triglyceride change in the liver as shown in Table 8 below, the triglyceride level in the ethanol group was 106.8±4.3 mg/g, which was insignificantly increased as compared with that in the control group, 76.4±6.5 mg/g. In addition, the triglyceride level in the ethanol+narirutin (300 mg/kg)-administered group was 76.2±4.0 mg/g, indicating that the triglyceride increment was insignificantly suppressed in the ethanol+narirutin (300 mg/kg)-administered group as compared with the ethanol group.

TABLE 8

|  | Control | Ethanol | Narirutin (150 mg/kg) | Narirutin (300 mg/kg) |
|---|---|---|---|---|
| Total Cholesterol (mg/g) | 70.3 ± 7.6$^a$ | 80.9 ± 5.2$^a$ | 73.8 ± 2.7$^a$ | 72.0 ± 1.7$^a$ |
| Triglycerides (mg/g) | 76.4 ± 6.5$^a$ | 106.8 ± 4.3$^b$ | 86.2 ± 4.1$^a$ | 76.2 ± 4.0$^a$ |

Superoxide dismutases (SOD) are metalloenzymes, and classified according to metal ions, which are contained therein, that is, Cu, Zn, Mn, and Fe. SOD protects the living body from oxidation stress since $O_2$ accepts one electron to convert incompletely oxidized $O^{2-}$ into $H_2O_2$, which is then excreted.

Figure 3:
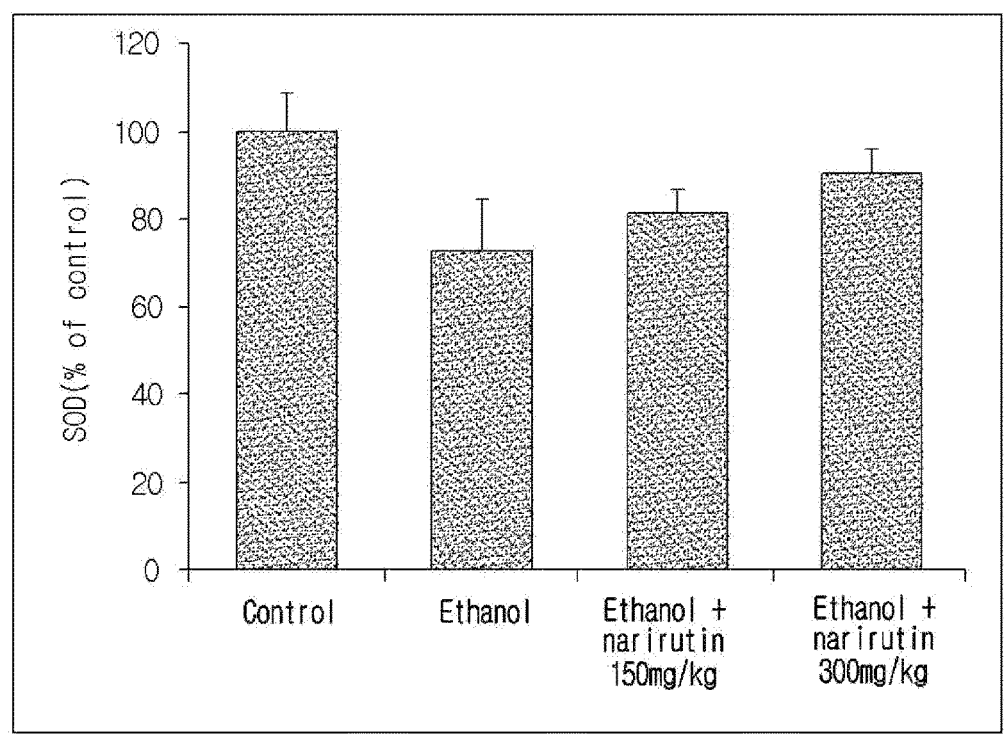
FIG. 3 is a graph showing SOD measurement results in livers of mice orally administered with narirutin according to an embodiment of the present invention.

Thus, the change in SOD activity by narirutin administration in an alcoholic liver disease animal model was measured to evaluate the liver protection effect of narirutin. SOD activity was observed to be lower in the alcohol-administered group than in the normal group (FIG. 3). The 300 mg/kg-narirutin treatment significantly increased the activity of antioxidant enzyme SOD in the liver tissue that was damaged due to ethanol. Therefore, it can be seen that the narirutin treatment significantly increased the activity of the superoxide $O^{2-}$ removal enzyme SOD, leading to a reduction in oxidation stress caused by ethanol, thereby protecting the liver.

Figure 4A:
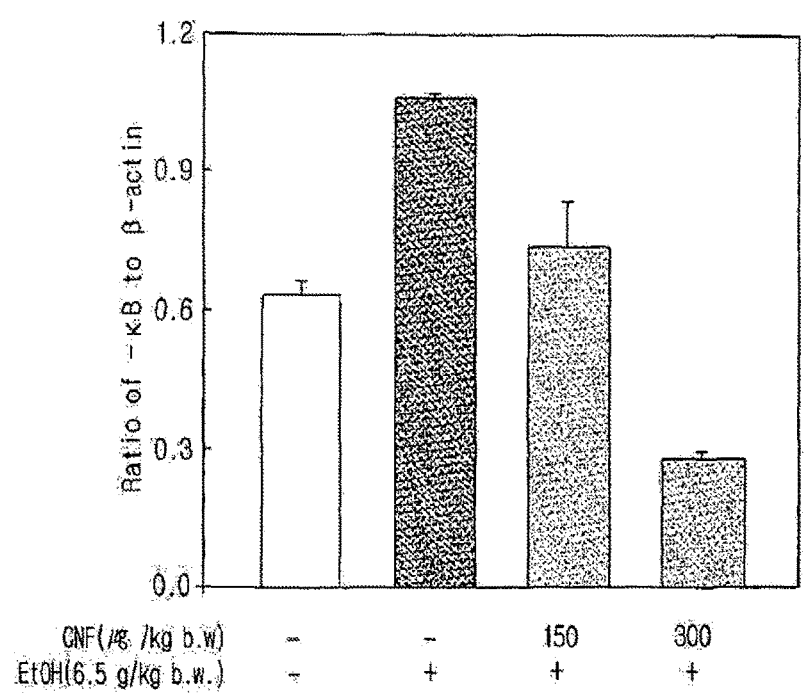
FIGS. 4A and B are SDS-PAGE images showing the effect of narirutin addition on the expression of NF-kB protein in the mouse liver.
Figure 4B:
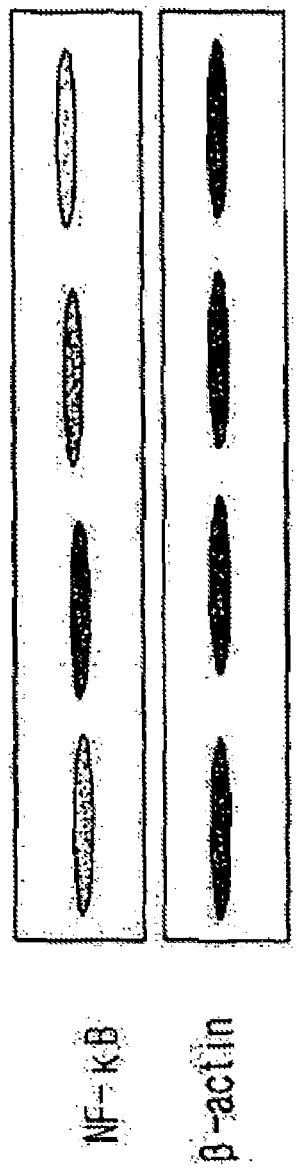

As observed in macrophagocytes, it can be seen that the expression of the inflammatory factor NF-κB was remarkably increased due to alcohol ingestion in the liver, and the narirutin ingestion was observed to inhibit the NF-κB expression in a dose-dependent manner (FIG. 4A and FIG. 4B). These results indicate that the narirutin ingestion can delay the initial revelation of liver diseases such as cirrhosis, liver fibrosis, and liver cancers, which are induced by chronic alcohol ingestion.

3.4 Hepatic Histology Through Liver Tissue Photographing

For histomorphometric analysis of liver tissues of mice subjected to long-term ethanol administration, Hematoxylin & Eosin and Masson's trichrome staining was performed. In the liver tissue shown in FIG. 5, the region excluding hepatic portal vein was stained red, and the nucleus was stained dark blue.

Figure 5:
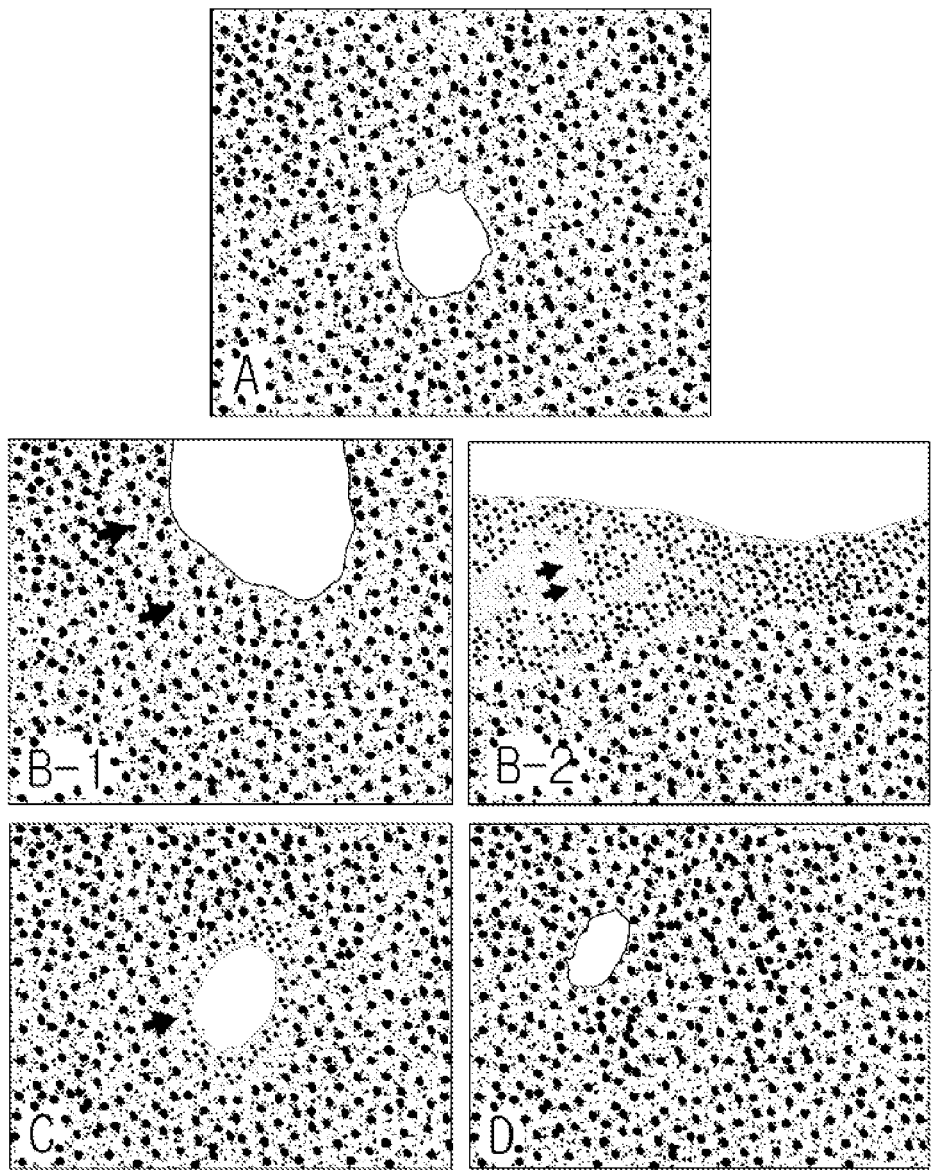
FIG. 5 depicts images showing the effect of narirutin on the liver damage inhibition in the liver tissues of mice administered with ethanol for 8 weeks according to an embodiment of the present invention. (A) a normal group; (B-1,2) an ethanol (6.5 g/kg b.w./day)-administered group; (C) a low-narirutin (150 mg/kg b.w.)-fed group; (D) a high-narirutin (300 mg/kg b.w.)-fed group. Hydropic degeneration (arrows), lymphoma increment (double arrow head), and cellular necrosis (double arrow) in the liver cells due to the long-term ethanol administration; Hematoxylin and eosin stain; Original magnification, ×100
Figure 6:
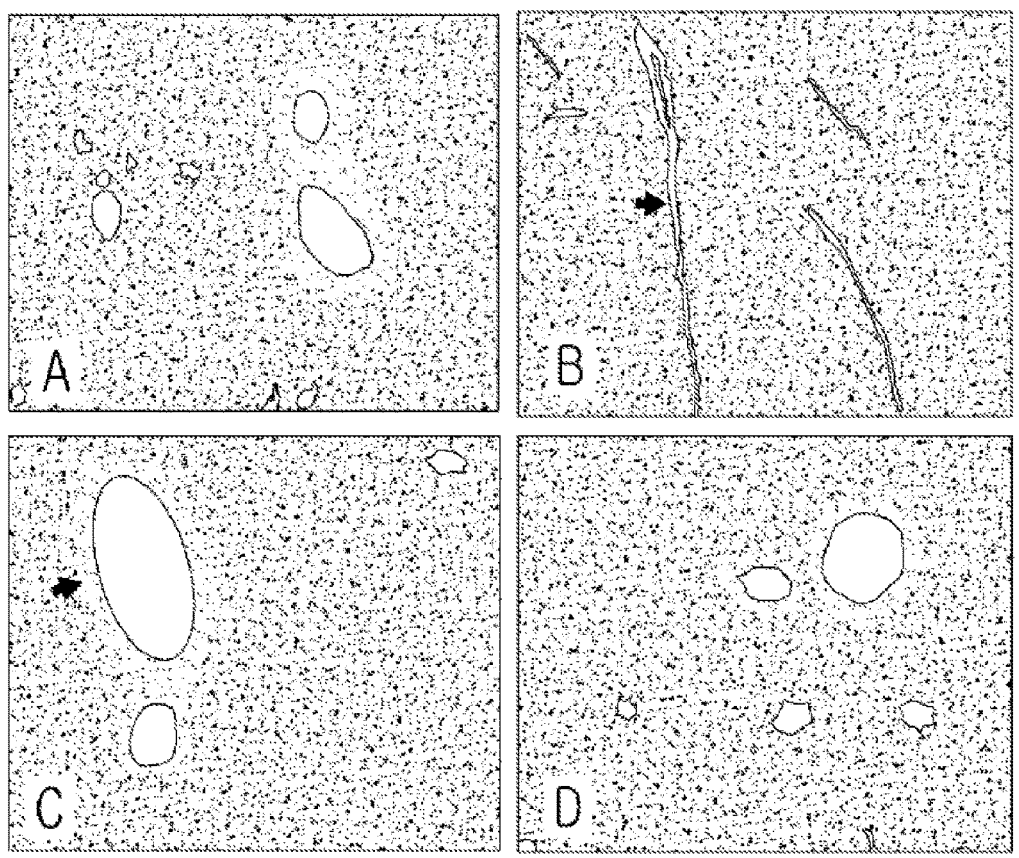
FIG. 6 depicts images showing the effect of narirutin on the fibrosis inhibition in liver tissues of mice administered with ethanol for 8 weeks according to an embodiment of the present invention. (A) a normal group; (B-1,2) an ethanol (6.5 g/kg b.w./day)-administered group; (C) a low-narirutin (150 mg/kg b.w.)-fed group; (D) a high-narirutin (300 mg/kg b.w.)-fed group. Fibrosis (double arrow head) and hydropic degeneration (arrow) due to the long-term ethanol administration; Masson's trichrome stain; Original magnification, ×100

In the normal group, the three-dimensional conformation of hepatic lobules was well maintained, both of the cytoplasm and the circular nucleus were obvious, fibrosis was not observed around hepatic portal vein and central veins, and hepatocellular necrosis and inflammation were not observed (FIG. 5A). Collagen was also not observed (FIG. 6A). In the ethanol-administered group, the three-dimensional conformation of hepatic lobules disappeared, and infiltration and lymphoma due to hepatocellular hydropic degeneration were increased around the hepatic portal vein (B-1 of FIG. 5), and hepatocellular necrosis was observed at the distal end region of the liver tissue (B-2 of FIG. 5). These are characteristic findings of fatty liver. In other words, fat and moisture are excessively accumulated in the liver cells, resulting in ballooning degeneration, and then leukocytes are increased in the hepatic lobules to remove debris of liver cells that were widely necrotized. Further, venous-venous fibrosis linkage and relatively rich collagen were observed around the hepatic portal vein and between the central veins (B of FIG. 6). After that, if the fibrosis progression is widespread, the liver tissue is expected to be replaced by strong connective tissue instead of normal hepatocytes, which finally leads to liver cirrhosis.

In the narirutin (150 mg/kg)-administered group, infiltration due to hepatocellular hydropic degeneration was somewhat observed around the hepatic portal vein and the central veins (C of FIG. 5), but hepatocellular necrosis and fibrosis not observed throughout the liver tissue (FIG. 6C). In the narirutin (300 mg/kg)-administered group, the three-dimensional conformation of hepatic lobules was well maintained and histological changes of the liver lesion due to long-term administration of ethanol were not observed. These results verify that the narirutin ingestion can effectively delay the progress into cirrhosis.

Accordingly, the narirutin extracted from citrus peel can be utilized as a material capable of preventing liver dysfunction due to acute or chronic alcohol intake, and can be used as a pharmaceutical composition or food composition having an effect of preventing liver diseases.

Example 4

Preparation of Citrus Fermented Milk

Citrus fermented milk was prepared by adding a secondary citrus peel extract instead of citrus juice to fermented yogurt before and after fermentation to contain high-concentration narirutin. The added amounts of narirutin were determined such that 200 ppm and 400 ppm of narirutin were contained in the final products. The experiment was performed on different periods for narirutin addition, before fermentation and after fermentation.

In the case of narirutin treatment before fermentation, crude oil, skim milk, and a flavonoid extract were added and mixed at 65° C. to be completely dissolved, followed by homogenization at a pressure of 180~250 $kgf/cm^2$. The resultant material was sterilized at 90° C. for 5 minutes and cooled to 90° C. Then, a commercial strain (ABT-D) was seeded therein at 0.1 wt %, and cultured until the final pH was decreased to 4.4. The cultured liquid was cooled to 90° C. while being stirred. Oligosaccharides, liquid fructose, and purified water were added and mixed with the fermented liquid, and then a container was filled with the mixture, followed by packaging and storing at a temperature of 5° C.

In the case of narirutin treatment after fermentation, crude oil and skim milk were added and then mixed at 65° C. to be completely dissolved, followed by homogenization at a pressure of 180~250 $kgf/cm^2$. The resultant material was sterilized at 90° C. for 5 minutes and cooled to 90° C. Then, a commercial strain (ABT-D) was seeded therein at 0.1 wt %, and cultured until the final pH was decreased to 4.4. The cultured liquid was cooled to 90° C. while being stirred. Oligosaccharides, liquid fructose, purified water, and a flavonoid extract were added and mixed with the fermented liquid, and then a container was filled with the mixture, followed by packaging and storing at a temperature of 5° C.

Meanwhile, to measure the chemical change of narirutin during the preparation of the citrus fermented milk, skim milk (3.85%) was mixed with crude milk (96.15%), followed by sterilization at 90° C. for 30 minutes, and then a 33° Brix concentrated citrus juice was added at 5%, followed by fermentation. Here, *Streptococcus thermophilus*, *Lactobacillus acidophilus*, ABT-L (mixture strain) were used as lactic acid bacteria. Results were shown in Table 9.

TABLE 9

|  | Narirutin (mM) |
|---|---|
| Control | 0.090 |
| *Streptococcus thermophilus* | 0.097 |
| *Lactobacillus acidophius* | 0.089 |
| ABT-L (Mixture strain) | 0.093 |

As shown in Table 9, it can be seen that, since narirutin remains intact without being converted into naringenin or the like during the fermentation, fermented milk containing narirutin can be prepared.

4.1 Preparation of Fermented Milk Added with Secondary Citrus Peel Extract at 5%

Table 10 below shows each composition when the secondary citrus peel extract was added at 0.5% of the total weight of each mixture.

TABLE 10

| | sample | | | | | |
|---|---|---|---|---|---|---|
| | A | B | C | D | E | F |
| Crude milk | 83.27 | 81.27 | 79.27 | 83.27 | 81.27 | 79.27 |
| Skim milk | 3.23 | 3.23 | 3.23 | 3.23 | 3.23 | 3.23 |
| oligosacharide | 2 | 2 | 2 | 2 | 2 | 2 |
| fructose | 5 | 5 | 5 | 5 | 5 | 5 |
| Strawberry jam | 6 | 8 | 10 | 6 | 8 | 10 |
| 2% narirutin extract | 0.5 | 0.5 | 0.5 | 0.5 | 0.5 | 0.5 |
| 2% narirutin extract addition | Before fermentation | | | After fermentation | | |
| Total | 100 | 100 | 100 | 100 | 100 | 100 |

As shown in Table 10 above, the sensory test was performed on the strawberry fermented milk prepared by adding a 2% narirutin extract at 0.5%, and the results were shown in Table 11 below.

TABLE 11

| | Appearance (color) | Taste | Texture feeling | Overall preference | Purchasing intension |
|---|---|---|---|---|---|
| control[1] | 6.00 ± 1.73$^{a2)}$ | 6.00 ± 1.00$^{ab}$ | 6.85 ± 1.34$^a$ | 6.54 ± 1.05$^a$ | 6.00 ± 1.22$^a$ |
| A | 6.77 ± 0.83$^a$ | 3.23 ± 0.83$^d$ | 5.85 ± 1.21$^a$ | 3.00 ± 0.71$^d$ | 2.54 ± 1.13$^c$ |
| B | 6.69 ± 1.11$^a$ | 4.46 ± 1.05$^c$ | 5.85 ± 1.34$^a$ | 4.38 ± 1.04$^c$ | 3.77 ± 1.54$^b$ |
| C | 6.69 ± 1.89$^a$ | 5.46 ± 2.22$^{bc}$ | 6.31 ± 1.97$^a$ | 5.31 ± 2.39$^{bc}$ | 5.23 ± 2.39$^a$ |
| D | 6.54 ± 1.39$^a$ | 5.54 ± 1.05$^b$ | 6.54 ± 0.88$^a$ | 6.00 ± 0.71$^{ab}$ | 5.31 ± 1.18$^a$ |
| E | 6.85 ± 1.14$^a$ | 6.69 ± 1.11$^a$ | 6.69 ± 1.32$^a$ | 7.00 ± 1.08$^a$ | 6.46 ± 1.33$^a$ |
| F | 6.69 ± 1.44$^a$ | 6.62 ± 1.33$^a$ | 6.69 ± 1.38$^a$ | 6.46 ± 1.51$^a$ | 6.31 ± 1.44$^a$ |

[1]Table-spoon Bulgaris from Namyang Dairy Products, strawberry-flavored product
[2]p > 0.05

As shown in Table 11 above, samples D, E, and F in which the 2% narirutin extract was added after fermentation showed more excellent results in overall preference than samples A, B, and C in which the 2% narirutin extract was added before fermentation. Sample D got a lower grade in overall preference than the control group. The reason seems to be that the bitterness of the 2% narirutin extract remains in the sample. However, the content of strawberry jam is raised to remove bitterness, leading to an increase in the preference. Since sample F exhibited a very strong sweetness, sample E is likely to be the most preferred product.

4.2 Preparation of Fermented Milk Added with Secondary Citrus Peel Extract at 1.0%

Table 12 below shows each composition when the secondary citrus peel extract was added at 1.0% of the total weight of each mixture.

TABLE 12

| | sample | | | | | |
|---|---|---|---|---|---|---|
| | A | B | C | D | E | F |
| Crude milk | 82.77 | 80.77 | 78.77 | 82.77 | 80.77 | 78.77 |
| Skim milk | 3.23 | 3.23 | 3.23 | 3.23 | 3.23 | 3.23 |
| oligosacharide | 2 | 2 | 2 | 2 | 2 | 2 |
| fructose | 5 | 5 | 5 | 5 | 5 | 5 |
| Strawberry jam | 6 | 8 | 10 | 6 | 8 | 10 |
| 2% narirutin extract | 1 | 1 | 1 | 1 | 1 | 1 |
| 2% narirutin extract addition | Before fermentation | | | After fermentation | | |
| Total | 100 | 100 | 100 | 100 | 100 | 100 |

As shown in Table 12 above, the sensory test was performed on the strawberry fermented milk prepared by adding a 2% narirutin extract at 1.0%, and the results were shown in Table 13 below.

TABLE 13

| | Appearance (color) | Taste | Texture feeling | Overall preference | Purchasing intension |
|---|---|---|---|---|---|
| control[1] | 7.23 ± 1.74$^{a2)}$ | 5.61 ± 1.04$^b$ | 6.23 ± 1.17$^a$ | 5.46 ± 1.27$^{bc}$ | 5.53 ± 1.27$^{abc}$ |
| A | 7.31 ± 1.03$^a$ | 3.46 ± 1.20$^c$ | 6.15 ± 1.34$^a$ | 3.85 ± 1.21$^d$ | 3.46 ± 1.39$^d$ |
| B | 7.15 ± 1.14$^a$ | 4.77 ± 1.24$^b$ | 6.31 ± 1.32$^a$ | 5.15 ± 1.14$^c$ | 4.62 ± 1.33$^c$ |
| C | 7.31 ± 1.03$^a$ | 5.46 ± 1.27$^b$ | 6.54 ± 1.05$^a$ | 5.46 ± 1.27$^{bc}$ | 5.46 ± 1.20$^{abc}$ |
| D | 7.00 ± 1.47$^a$ | 5.23 ± 1.36$^b$ | 6.23 ± 1.17$^a$ | 5.15 ± 1.21$^c$ | 5.15 ± 2.03$^{abc}$ |
| E | 7.00 ± 1.29$^a$ | 5.77 ± 1.2$^{ab}$ | 6.62 ± 1.04$^a$ | 6.23 ± 0.93$^{ab}$ | 5.85 ± 1.41$^{ab}$ |
| F | 7.38 ± 0.87$^a$ | 6.69 ± 1.03$^a$ | 6.69 ± 0.95$^a$ | 6.77 ± 0.83$^a$ | 6.54 ± 1.05$^a$ |

[1]Table-spoon Bulgaris from N Dairy Products, strawberry-flavored product
[2]p > 0.05

As shown in Table 13 above, the preference was shown to be higher in samples in which the 2% narirutin extract was added after fermentation than in samples in which the 2% narirutin extract was added before, which were the same with the results obtained by the addition of the 2% narirutin extract at 0.5%. However, the preference was shown to be higher in sample C than in sample D, and the reason seems to be that a high content of strawberry jam removed bitterness in sample C. The reason that sample F received the highest preference is determined to be that bitterness slightly remains in sample E.

The above fermented milk preference survey results suggest that sample E shows the highest preference among samples in which the 2% narirutin extract was added at 0.5%.

The composition containing a material according to the present invention may be formulated as an oral dosage form, such as a powder, granule, tablet, capsule, suspension, emulsion, syrup, or an aerosol, an external preparation, a suppository, or a sterile injectable solution, according to the general method for each case. Specifically, the composition may be formulated by using a diluent or vehicle, such as a filler, extender, binder, wetting agent, disintegrant, or surfactant. Solid preparations for oral administration include a tablet, a pill, a powder, a granule, a capsule, and the like. These solid preparations may be prepared by mixing the extract with at least one vehicle, for example, starch, calcium carbonate, sucrose, lactose, gelatin, or the like. In addition, lubricants such as magnesium stearate and talc may be used beside a simple vehicle. Liquid preparations for oral administration include a suspension, a preparation for internal application, an emulsion, a syrup, and the like. Besides simple diluents such as water, liquid, and paraffin, several vehicles, for example, a wetting agent, a sweetener, an aroma, and a preservative may be contained therein. Preparations for parenteral administration include a sterilized aqueous solution, a water-insoluble excipient, a suspension, an emulsion, a lyophilized formulation, and a suppository. As the water-insoluble excipient or suspension, propylene glycol, polyethylene glycol, vegetable oil such as olive oil, or injectable ester such as ethylolate may be used. As a substrate for the suppository, Witepsol, Macrogol, twin 61, cacao butter, laurin butter, or glycerogelatin may be used.

Although the dosage of the extract of the present invention may vary according to age, gender, and body weight of patients, the extract may be administered in an amount of generally 0.01 to 500 mg/kg and preferably 0.1 to 100 mg/kg once a day or divided into multiple doses. In addition, the dosage of the extract may be increased or decreased according to an administration route, severity of disease, gender, body weight, age, and the like. Therefore, the above dosage range is not intended to restrict the scope of the present invention.

The present invention is directed to a composition for inhibiting hepatic dysfunction, containing a citrus peel extract or narirutin as an active ingredient, and a method for extracting narirutin from citrus peel, and is industrially applicable.

The invention claimed is:

1. A pharmaceutical composition for treating or preventing alcoholic liver diseases, the composition comprising a citrus peel extract containing narirutin as an active ingredient, flavored fermented milk, and at least one vehicle,
   wherein the narirutin comprises 4% to 75% content in the citrus peel extract, and
   wherein the citrus peel extract containing narirutin is between 0.5-1% of the composition.

2. The composition of claim 1, wherein the composition is an orally administrable composition.

3. The composition of claim 1, wherein the composition is used in the form of a concentrate, a tablet, a hard capsule, or a soft capsule.

4. A food composition for improving alcoholic liver diseases, the composition comprising a citrus peel extract containing narirutin as an active ingredient, flavored fermented milk, and at least one vehicle,
   wherein the narirutin comprises 4% to 75% content in the citrus peel extract, and
   wherein the citrus peel extract containing narirutin is between 0.5-1% of the composition.

5. A method for treating or preventing alcoholic liver diseases, comprising: administering a pharmaceutical composition including an effective amount of a citrus peel extract containing narirutin as an active ingredient, flavored fermented milk, and at least one vehicle to a subject in need thereof,
   wherein the narirutin comprises 4% to 75% content in the citrus peel extract, and
   wherein the citrus peel extract containing narirutin is between 0.5-1% of the composition.

* * * * *